United States Patent [19]

Sumner, Jr. et al.

[11] Patent Number: 4,791,224

[45] Date of Patent: Dec. 13, 1988

[54] PROCESS FOR PREPARATION OF AN OXYACETIC ACID/HYDROXYETHYL ETHER COMPOUND

[75] Inventors: Charles E. Sumner, Jr., Kingsport; Eric J. Fugate, Jonesborough, both of Tenn.

[73] Assignee: Eastman Kodak Company, Rochester, N.Y.

[21] Appl. No.: 178,702

[22] Filed: Apr. 7, 1988

[51] Int. Cl.$^4$ .............................................. C07C 51/16
[52] U.S. Cl. ..................... 562/421; 562/471
[58] Field of Search ................. 562/421, 471

[56] References Cited

U.S. PATENT DOCUMENTS

| 2,930,801 | 3/1960 | Montagna et al. | 502/421 |
| 4,238,625 | 12/1980 | Fiege et al. | 562/421 |
| 4,532,346 | 7/1985 | Rehn et al. | 562/471 |

FOREIGN PATENT DOCUMENTS

| 0011793 | 6/1980 | European Pat. Off. |
| 0073545 | 3/1983 | European Pat. Off. |
| 2010233 | 1/1977 | Japan. |
| 3139727 | 6/1978 | Japan. |

*Primary Examiner*—Paul J. Killos
*Attorney, Agent, or Firm*—Charles R. Martin; William P. Heath, Jr.

[57] ABSTRACT

Process for the preparation of an aryloxyacetic acid/hydroxyethyl ether by oxidation of aryloxyethanol of the formula:

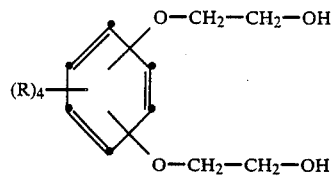

wherein R either individually or independently of one another represents hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring, in an aqueous alkaline reaction medium at a temperature in the range of 0° C. to the boiling point of the reaction medium in the presence of a catalytic amount of a catalyst comprised of palladium, bismuth, and carbon in the presence of a phenol corresponding to the structure:

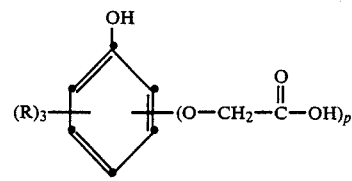

wherein R is as described above and p is 0, 1 or 2, to form the corresponding alkali metal ester/hydroxyethyl ether after catalyst removal the alkali metal ester is contacted with a mineral acid.

9 Claims, No Drawings

PROCESS FOR PREPARATION OF AN OXYACETIC ACID/HYDROXYETHYL ETHER COMPOUND

The invention relates to a process for the preparation of an oxyacetic acid/hydroxyethyl ether compound by oxidation of an aryloxyethanol in the presence of a phenol.

The oxidation of aryloxyethanols to corresponding acids is well known in the art. For example U.S. Pat. No. 4,238,625 discloses that a compound having the structure

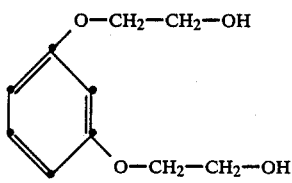

can be oxidized to the corresponding dicarboxylic acid having the structure

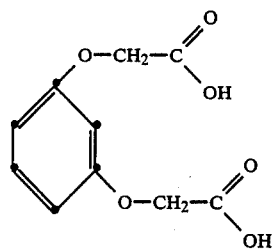

We have now discovered that an aryloxyethanol, such as resorcinol bis($\beta$-hydroxyethyl) ether corresponding to the structure

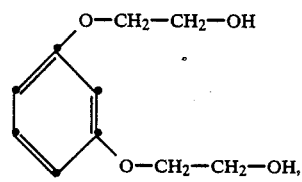

can be oxidized such that only one of the two hydroxyl groups is converted to a carboxylic acid to form what can be thought of as an oxyacetic acid/hydroxylethyl ether compound corresponding to the structure

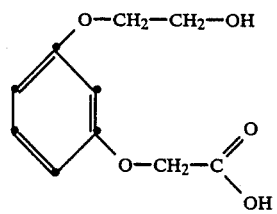

According to our invention the oxidation is conducted in the presence of a phenol compound corresponding to a specific structure.

The process of our invention is composed of three steps. In the first step the aryloxyethanol is oxidized in the presence of a phenol to the corresponding alkali metal oxyacetate/hydroxyethyl ether using a catalyst comprised of carbon, palladium and bismuth. The next step is to separate the alkali metal oxyacetate/hydroxyethyl ether from the catalyst. The oxyacetic acid/hydroxyethyl ether compound is then prepared by contacting the alkali metal oxyacetate/hydroxyethyl ether with a mineral acid.

The process of this invention can be illustrated by reference to a preferred embodiment. In this embodiment resorcinol bis($\beta$-hydroxyethyl)ether having the structure

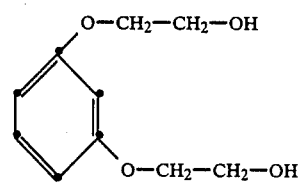

is contacted with oxygen in an aqueous alkaline reaction medium at a temperature range from 0° C. to the boiling point of the reaction medium in the presence of a catalytic amount of a catalyst comprised of palladium, bismuth and carbon in the presence of a phenol corresponding to the structure

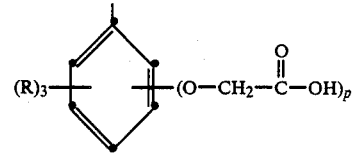

wherein R is hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring, and p is 0, 1 or 2.

The oxidation product is a sodium oxyacetate/hydroxyethyl ether which can be though of as the half sodium ester of 1,3-phenylenedioxydiacetic acid corresponding to the structure

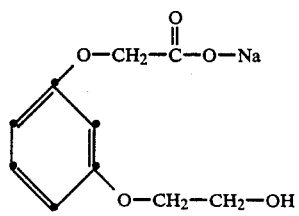

This material is then separated by filtration from the catalyst. The material is then contacted with a mineral acid to prepare the corresponding acid corresponding to the structure

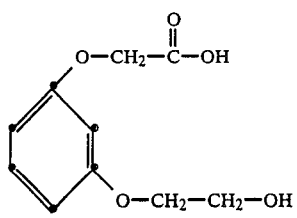

Broadly the oxyacetic acid/hydroxyethyl ether compound prepared by the process of this invention corresponds to the structure

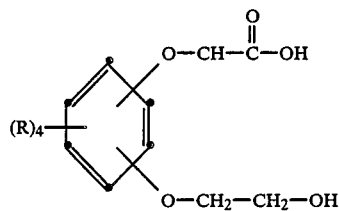

wherein R is the same as described earlier.

Alkyl radicals can be straight-chain or branched hydrocarbon radicals with 1 to 12, preferably 1 to 6, carbon atoms. Preferred alkyl radicals for the process according to the invention are lower alkyl radicals. Examples of alkyl radicals which may be mentioned are methyl, ethyl, propyl, isopropyl, butyl, isobutyl, sec.-butyl, tert.-butyl, pentyl, isopentyl, tert. amyl, hexyl, isohexyl, heptyl, isoheptyl, tert.-octyl, isooctyl, nonyl, isononyl, decyl, isodecyl, undecyl, isoundecyl, dodecyl and isododecyl.

Cycloalkyl radicals can be cyclic hydrocarbon radicals with 4 to 9, preferably 5 and 6, carbon atoms. The cyclopentyl and the cyclohexyl radical may be mentioned as examples.

The phenyl and the naphthyl radical may be mentioned as preferred aryl radicals for the process according to the invention.

Aralkyl radicals can be alkyl radicals with 1 to 6 carbon atoms, preferably lower alkyl radicals, which are substituted by an aromatic hydrocarbon radical with 6 to 12 carbon atoms, preferably phenyl and naphthyl. Benzyl, α,α-dimethyl-benzyl groups may be mentioned by way of example.

Alkoxy radicals can consist of up to 12, preferably of up to 6, carbon atoms in the aliphatic part. A lower alkoxy radical is particularly preferred. The following may be mentioned as examples of alkoxy radical: methoxy, ethoxy, propoxy, isopropoxy, butoxy, isobutoxy, tert-butoxy, pentoxy, isopentoxy, hexoxy, isohexoxy and methylenedioxy.

The cyclopentoxy and the cyclohexoxy radical may be mentioned as preferred cycloalkoxy radicals.

The phenoxy and the naphthoxy radical may be mentioned as preferred aryloxy radicals.

Halogens can be fluorine, chlorine, bromine and iodine, preferably chlorine and bromine.

Lower alkylcarbonyl radicals ($C_1$ to $C_6$), such as the acetyl radical, may be mentioned as preferred alkylcarbonyl radicals.

The benzoyl radical may be mentioned as a preferred arylcarbonyl radical.

Fusion of a benzene ring to the phenyl ring can, for example, produce the naphthalene ring system.

Fusion of a cycloalkane ring to the phenyl ring can, for example, produce the tetraline ring system.

It is of course possible for the above mentioned substituents to be substituted by usual radicals which are inert under the reaction conditions. Fluorine, chlorine, methyl and methoxy may be mentioned as examples.

One preferred embodiment is where n is 4 and R is hydrogen. A particular preferred embodiment is the meta isomer.

The aryloxyethanols are prepared by methods well known in the art. For example, the aryloxyethanols can be prepared by addition reaction of ethylene oxide with the hydroxyl group or groups of an appropriately substituted phenol or naphthol.

Representative examples of aryloxyethanols are resorcinol bis(β-hydroxyethyl)ether; hydroquinone bis(β-hydroxyethyl)ether; 2,6-dihydroxynaphthalene bis(β-hydroxyethyl)ether; 2,7-dihydroxynaphthalene bis(β-hydroxyethyl)ether; 5-chloro resorcinol bis(β-hydroxyethyl)ether; and chlorohydroquinone bis(β-hydroxyethyl)ether.

The first step of the invention is conducted in the presence of a phenol corresponding to the structure:

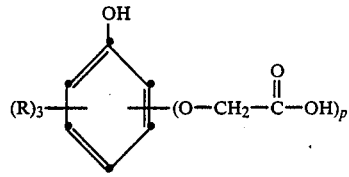

wherein R is as described above and p is 0, 1 or 2.

Examples of phenols which can be used in this invention are 3-hydroxyphenoxy acetic acid, 4-hydroxyphenoxy acetic acid, hydroxynaphthoxy acetic acid. A preferred embodient is (3-hydroxy)phenoxy acetic acid. The first step of the process of this invention is conducted by bringing oxygen or a oxygen-containing gas, such as air, into good contact with the aryloxyethanol in an aqueous medium, which also contains the source of the alkali metal cation and the catalyst. The reaction medium can be a solution or a suspension; however, a solution is preferred.

In general, the reaction is carried out at atmospheric pressure, but oxidation can also be carried out at higher or lower pressures. In general, the process according to the invention is carried out in the pressure range of 0.5 to 10 bar. The alkali metal oxyacetate hydroxyl ether compound which results from the first step of the invention corresponds to the structure:

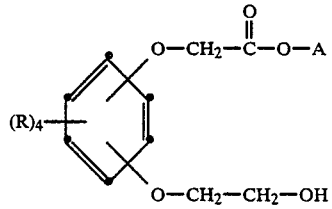

wherein R is as described above and A is an alkali metal cation.

It is important that the catalyst be separated from the aryloxyacetate/hydroxyethyl ether. This can be accomplished by method well known in the art, such as centrifugation or filtration. Due to cost, filtration is preferred.

The alkali metal oxyacetate/hydroxyethyl ether which is separated from the catalyst is then converted into the corresponding acid by contact with a mineral acid according to techniques well known in the art, such as disclosed in U.S. Pat. No. 4,238,625.

The palladium useful in the catalyst of this invention can be in a variety of forms. Elemental palladium metal can be used. Other palladium compounds, such as the oxides can be used.

The bismuth useful in this invention can be in a variety of forms such as described in U.S. Pat. No. 4,238,625. The metals to be used as activators, particularly bismuth and/or lead or silver, according to the invention can be employed in the elemental form and/or in the form of their compounds, for example as oxides, hydroxides, salts of hydracids, such as chlorides, bromides, iodides, sulphides, selenides and telurides, or as salts of inorganic oxy-acids, such as nitrates, nitrites, phosphites, sulfates, phosphates, carbonates, perchlorates, antimonates, arsenates, selenites, selenates and borates, or as salts of oxy-acids of the transition metals, such as vanades, niobates, tentalates, chromates, molybdates, tunstates and permanganates, or as salts of organic aliphatic or aromatic acids, such as, for example, formates, acetates, propionates, benzoates, salicylates, lactates, aryloxyacetates and citrates, when cadmium is additionally present it can be present in elemental form or in the form of a compound thereof, including any of the types of compounds named above. Preferred forms are nitrate, nitrilotriacetate, oxides with nitrate being the most preferred.

The carbon useful for the catalyst support is a low sulfur, pophilic, pulverulent type, which is high in silicon and has an ordered structure. Materials of this nature are well known in the art.

The relative amounts of metals in the catalyst can vary widely. Broadly, the mole ratio of bismuth to palladium can be 0.05 to 1.0 moles of bismuth per mole of palladium. Preferably the ratio is 0.05 to 0.5 and more preferably 0.1 to 0.2.

The catalyst useful in this invention is prepared by applying the metals to a carbon support according to methods well known in the art. For example: An aqueous slurry of 5 weight percent Pd on carbon is reduced with hydrogen at 85° C. The appropriate amount of bismuth is added as a solid or as an aqueous solution after the hydrogen has been purged from the slurry with nitrogen. The slurry is let cool to about 40° then filtered. The resulting catalyst is washed with water and stored wet. Alternatively, the aqueous slurry can be used as is.

The amount of catalyst can vary within wide limits depending on the desired rate of oxidation. In general, the amount of catalyst is 0.5 to 10 weight percent, preferably 1 to 5 weight percent, based on the weight of aryloxyethanol.

Preferably the steps of the process are performed in the sequence described; however, the sequence of the steps can be modified if desired. For example, the catalyst can be added to the mixture or solution containing aqueous alkali metal and aryloxyethanol. One can also add the mixture of aqueous alkali and aryloxyethanol to the catalyst. Finally, one can also first take the catalyst, a part of the aqueous alkali metal solution and then add the aryloxyethanol together with the remaining alkali metal solution.

The oxidation step of the process of the invention is carried out in an aqueous alkaline reaction medium. Sodium hydroxide or potassium hydroxide are preferred compounds to prepare the alkali reaction medium. The amount of alkali metal cation is chosen so as to provide 1 to 6 mols of alkali metal cation per mol of carboxy group formed.

The concentration of the aryloxyethanol in the aqueous alkaline reaction mixture is in general selected so that the resulting aryloxyacetic acid is present in solution during the reaction. Concentrations of 2% to 25% by weight are advantages. If desired, the solubility can be improved by the addition of inert solvents or solubilizing agents.

The temperature for the oxidation step can lie between 0° C. and the boiling point of the reaction mixture. The reaction temperature to be used in each individual case depends on the catalyst system, the alkali concentration, the material properties of the educts and of the products, and other factors. The temperature range of about 70° C. to about 100° C. is preferred and the range of 80° C. to 90° C. is particularly preferred.

The oxyacetic acid/hydroxylethyl ether compounds prepared by this invention are useful for the preparation of high molecular weight polyesters.

EXAMPLE

Resorcinol bis($\beta$-hydroxyethyl)ether (100 g 0.51 mol) was dissolved in 1 liter of water containing NaOH (44 g 1.1 mol) and (3-hydroxy)phenoxy acetic acid (25 g 0.15 mol). The solution was warmed to 60° to dissolve all of the ether and 5% Pd on carbon (10 g) and bismuth nitrate pentahydrate (0.302 g) were added. The resulting slurry was transferred to a 2-liter, stirred autoclave which can be operated at pressures from 25 to 350 psig and temperatures from 50° to 200° C. and is agitated by a magnetic stirrer equipped with a turbine. The autoclave was equipped with a dip tube which allowed the reaction mixture to be sampled periodically while the reaction was taking place. The mixture was stirred at 990 rpms while air was passed through the mixture at a rate of 4 slm at a pressure of 50 psig. The autoclave was slowly heated to 78° C. at which point an exotherm occurred, and the autoclave was cooled at such a rate to maintain the temperature of the reaction mixture at 78° to 82° C. After 1 hour, the temperature of the mixture dropped and the consumption of oxygen ceased. The mixture was removed from the autoclave, the catalyst was filtered off, and the filtrate was acidified with 150 mL of 20% sulfuric acid. After cooling to room temperature (about 2 hours), the product was collected by filtration, washed with cold water (200 mL), and dried in a vacuum oven at 40°. Of the 100 g of resorcinol bis($\beta$-hydroxyethyl)ether, 84 g were converted to the corresponding oxyacetic acid/hydroxylethyl ether.

I claim:

1. A process for the preparation of an oxyacetic acid/hydroxyethyl ether compound corresponding to the structure:

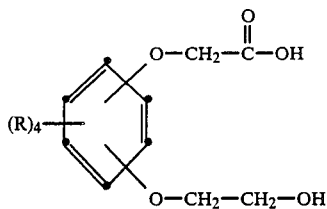

wherein R either individually or independently of one another represents hydrogen, alkyl, cycloalkyl, aryl, aralkyl, alkoxy, cycloalkoxy, aryloxy, halogen, alkylcarbonyl, arylcarbonyl, carboxyl or nitro, or represents a benzene ring fused to the phenyl ring, comprising (a) preparing an alkali metal oxyacetate/hydroxyethyl ether compound corresponding to the structure:

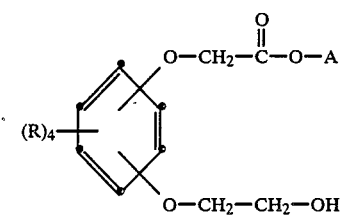

wherein R is as described above and A is an alkali metal cation, by contacting an aryloxyethanol corresponding to the structure:

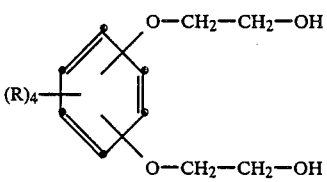

wherein R is as described above with oxygen in an aqueous alkaline reaction medium at a temperature range from 0° C. to the boiling point of the reaction medium in the presence of a catalytic amount of a catalyst comprised of palladium, bismuth and carbon in the presence of a phenol corresponding to the structure:

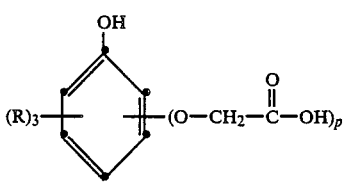

wherein R is as described above and p is 0, 1 or 2, (b) separating the oxyacetate/hydroxyethyl ether compound from the catalyst, and (c) preparing the oxyacetic acid/hydroxyethyl ether compound acid by contacting the separated oxyacetate/hydroxyethyl ether compound with a mineral acid.

2. The process of claim 1 wherein R is hydrogen or a benzene ring fused to the phenyl ring.

3. The process of claim 1 wherein the pH is greater than 10.

4. The process of claim 1 wherein the temperature range is from about 80° to about 100° C.

5. The process of claim 1 wherein the amount of catalyst is 0.5 to 10 weight percent, based on the weight of the aryloxyethanol.

6. The process of claim 5 wherein the amount of catalyst is 1 to 5 weight percent, based on the weight of the aryloxyethanol.

7. The process of claim 1 wherein the mole ratio of bismuth to palladium is 0.05 to 1.0:1.

8. The process of claim 7 wherein the mole ratio of bismuth to palladium is 0.05 to 0.5:1.

9. A process for the preparation of an oxyacetic acid/hydroxyethyl ether compound corresponding to the structure:

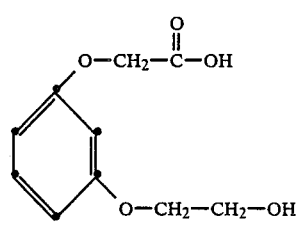

comprising (a) preparing a sodium oxyacetate/hydroxyethyl ether compound corresponding to the structure:

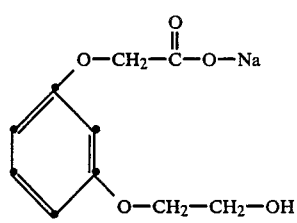

by contacting an aryloxyethanol corresponding to the structure:

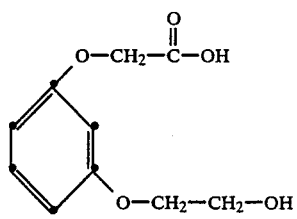

with oxygen in an aqueous alkaline reaction medium having a pH greater than 10 at a temperature in the range of 80° to 100° C. in the presence of from 2 to 3 weight percent, based on the weight of the aryloxyethanol, of a catalyst comprised of palladium, bismuth and carbon wherein the mole ratio of bismuth to palladium is about 0.1 to 0.2:1 in the presence of a phenol corresponding to the structure:

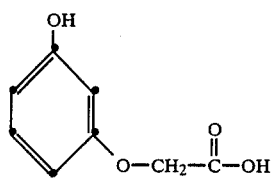

(b) separating by filtration the oxyacetate/hydroxyethyl ether compound from the catalyst, and
(c) preparing the oxyacetic acid/hydroxyethyl ether compound acid by contacting the separated oxyacetate/hydroxyethyl ether compound with a mineral acid.

* * * * *

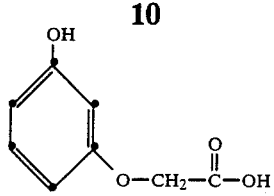

(b) separating by filtration the oxyacetate/hydroxyethyl ether compound from the catalyst, and
(c) preparing the oxyacetic acid/hydroxyethyl ether compound acid by contacting the separated oxyacetate/hydroxyethyl ether compound with a mineral acid.

* * * * *